United States Patent [19]
Ecker et al.

[11] Patent Number: 6,034,233
[45] Date of Patent: Mar. 7, 2000

[54] 2'-O-ALKYLATED OLIGORIBONUCLEOTIDES AND PHOSPHOROTHIOATE ANALOGS COMPLEMENTARY TO PORTIONS OF THE HIV GENOME

[75] Inventors: David Ecker, Carlsbad; Timothy A. Vickers, Vista, both of Calif.

[73] Assignee: Isis Pharmaceuticals Inc., Carlsbad, Calif.

[21] Appl. No.: 07/794,396

[22] Filed: Nov. 19, 1991

Related U.S. Application Data

[63] Continuation-in-part of application No. 07/578,929, May 4, 1990, abandoned, and application No. PCT/US91/02558, Apr. 15, 1991.

[51] Int. Cl.[7] .................................................. C07H 21/00
[52] U.S. Cl. ............................................ 536/24.5; 514/44
[58] Field of Search ............................. 536/24.5; 514/44

[56] References Cited

U.S. PATENT DOCUMENTS

| | | | |
|---|---|---|---|
| 4,806,463 | 2/1989 | Goodchild et al. | 435/5 |
| 5,166,195 | 11/1992 | Ecker | 514/44 |
| 5,264,423 | 11/1993 | Cohen et al. | 514/44 |
| 5,276,019 | 1/1994 | Cohen et al. | 514/44 |
| 5,455,158 | 10/1995 | Vogel et al. | 435/7.21 |
| 5,474,935 | 12/1995 | Chatterjee et al. | 435/320.1 |

FOREIGN PATENT DOCUMENTS

| | | |
|---|---|---|
| 0331939 | 9/1989 | European Pat. Off. . |
| 0339842 | 11/1989 | European Pat. Off. . |
| 0386563 | 9/1990 | European Pat. Off. . |
| 331939 | 9/1990 | European Pat. Off. . |
| 386563 | 9/1990 | European Pat. Off. . |
| 0389802 | 10/1990 | European Pat. Off. . |
| 3907562 | 9/1990 | Germany . |
| 8703451 | 6/1987 | WIPO . |
| WO91/00243 | 1/1991 | WIPO . |
| WO-91/04753 | 4/1991 | WIPO . |
| 9117246 | 11/1991 | WIPO . |
| 9202228 | 2/1992 | WIPO . |

OTHER PUBLICATIONS

Jacks et al, "Characterization of Ribosomal Frameshifting in HIV–1 'gag–pol' Expression", Nature, vol. 331, No. 21, pp. 280–283, 1988.
Dayton et al., "Functional Analysis of CAR, the Target Sequence for the Rev Protein of HIV–1", Science, vol. 246, pp. 1625–1629, Dec. 1989.
Agrawal et al., *Proc. Natl. Acad. Sci. USA* 85:7079 (1988).
Agrawal et al., *Proc. Natl. Acad. Sci. USA* 86:7790 (1989).
Arnott and Selsing, *J. Mol. Biol.* 88:509 (1974).
Berkhout et al., *Cell*, 59:273 (1989).
Broitman et al., *Proc. Natl. Acad. Sci USA* 84:5120 (1987).
Casey et al., *Science* 240:924 (1988).
Dayton et al., *Science* 246:1625 (1989).
Feng and Holland, *Nature* 334:165 (1988).
Garcia et al., *EMBO J.*, 87:765 (1989).
Goodchild et al., *Proc. Natl. Acad. Sci. USA* 85:5507 (1988).
Hanvey et al., *Proc. Natl. Acad. Sci. USA* 85:6292 (1988).
Haseltine and Wong–Staal, *Scientific American*, 52 (Oct., 1988).
Henthorn et al., *Proc. Natl. Acad. Sci. USA* 85:6342 (1988).
Jaeger et al., *Proc. Natl. Acad. Sci. USA* 86:7706 (1989);.
Larson and Sells, *Mol. Cell. Biochem.* 74:5 (1987).
Laspia, et al., *Cell*, 59:283 (1989).
Le et al., *Nucl. Acids Res.* 16:5153 (1988).
Letsinger, *Proc. Natl. Acad. Sci. USA* 86:6553 (1989).
Loose–Mitchell, *TIPS*, 9:45–47 (1988).
Malter, *Science* 246:664 (1989).
Marcus–Sekura, *Anal. Biochemsitry*, 172:289–295 (1988).
Matsukura et al, *Proc. Natl. Acad. Sci. USA* 84:7706 (1987).
Mori et al., *Nucleic Acids Res.* 17:8027 (1989).
Resnekov et al., *J. Biol. Chem.* 264:9953 (1989).
Ratner et al., *Nature* 313:277 (1985).
Sharp and Marciniak, *Cell*, 59:229 (1989).
Stevenson and Iversen, *J. Gen. Virol.* 70:2673 (1989).
Shibahara et al., *Nucl. Acids Res.* 17:239 (1989).
Stein & Cohen, *Cancer Research*, 48:2659–2668 (1988).
Sarin et al., *Proc. Natl. Acad. Sci. USA* 85:7448 (1988).
Tinoco, Jr. et al., *Cold Spring Harb. Symp. Quant. Biol.* 52:135 (1987).
Tuerk et al., *Proc. Natl. Acad. Sci. USA* 85:1364 (1988).
Turner and Sugimoto, *Annu. Rev. Biophys. Biophys. Chem.* 17:167 (1988).
Van der Krol et al., *BioTechniques*, 6:958–973 (1988).
Walder, *Genes & Development*, 2:502–504 (1988).
Zaia et al., *J. Virol.* 62:3914 (1988).
Zamecnik et al., *Proc. Natl. Acad. Sci. USA* 83:4143 (1986).
Zon, *Journal of Protein Chemsitry*, 6:131–145 (1987).
Zon, *Pharmaceutical Research*, 5:539–549 (1988).
Guo et al., "Sequence Analysis of Original HIV–1," *Nature*, 348, 745–746 (1991).
Chang et al., "Inhibition of Rous Sarcoma Virus Replication by Antisense RNA," *J. Virology*, 61(3), 921–924 (1987).
Scheit, *Nucleotide Analogs, Synthesis and Biological Function*, Wiley–Interscience, 1980, New York, pp. 171–172.
McCune et al., "The SCID–hu Mouse: Murine Model for the Analysis of Human Hematolymphoid Differentiation and Function," *Science*, 241, 1632–1639 (1988).
Namikawa et al., "Infection of the SCID–hu Mouse by HIV–1," *Science*, 242, 1684–1686 (1988).
"Antisense Antiviral Drug in Clinical Trials," *Antiviral Agent Bulletin*, 5(6), 161–163 (1992).
"Antisense HPV Drug Enters Phase II Trials," *Antiviral Agent Bulletin*, 5(12), xx–xx (1992).

(List continued on next page.)

*Primary Examiner*—L Eric Crane
*Attorney, Agent, or Firm*—Law Offices of Jane Massey Licata

[57] ABSTRACT

Methods of modulating the activity of the TAR element of HIV are provided. Oligonucleotides having 6 to 50 bases and at least one 2'-O alkyl modification and selected sequences are disclosed.

7 Claims, 9 Drawing Sheets

OTHER PUBLICATIONS

*BioWorld Today,* Dec. 20, 1993, see p. 3, column 2, paragraphs following first bullet.

"ISIS 2105 Clarification," *Antiviral Agent Bulletin,* 6(2), 42–43 (1993).

Offensperger et al., "In vivo Inhibition of Duck Hepatitis B Virus Replication and Gene Expression by Phosphorothioate Modified Antisense Oligonucleotides," *EMBO J.,* 12(3), 1257–1262 (1993).

Simons et al., "Antisense c–myb Oligonucleotides Inhibit Intimal Arterial Smooth Muscle Cell Accumulation in vivo" *Nature,* 359, 67–70 (1992).

Burch et al., "Oligonucleotides Antisense to the Interleukin 1 Receptor mRNA Block the Effects of Interleukin 1 in Cultured Murine and Human Fibroblasts and in Mcie," *J. Clinical Invest.,* 88, 1190–1196 (1991).

Kitajima et al., "Ablation of Transplanted HTLV–1 Tax–Transformed Tumors in Mice by ANtisense Inhibition of NF–κB," *Science,* 258, 1792–1795 (Dec. 11, 1992).

Higgins et al., "Antisense Inhibition of the p65 Subunit of NFκB Blocks Tumorigenicity and Causes Tumor Regression," *Proc. Nat. Acad. Sci. USA* 90, 9901–9905 (1993).

Vlassov, "Inhibition of Tick–Borne Viral Encephalitis Expression Using Covalently Linked Oligonucleotide Analogs," reported at the conference entitle *Oligonucleotides As Antisense Inhibitors of Gene Expression: Therapeutic Implications,* Nat. Cancer Inst & Nat. Inst. Allergy & Infectious Diseases co–sponsors, Rockville, MD, Jun. 18–21, 1989, see Abstract supplied.

Cohen et al., "The New Genetic Medicines—Synthetic Strands of DNA Are Being Developed as Drugs. Called Antisense and Triplex Agents, They Can Potentially Attack Viruses and Cancers Without Harming Healthy Tissue," *Scientific American,* pp. 76–82, Dec. 1994.

Mirabelli et al., "In Vitro and In Vivo Pharmacologic Activities of Antisense Oligonucleotides," *Anti–Cancer Drug Design,* 6, 647–661 (1991).

*Goodman and Gilman's The Pharmacological Basis of Therapeutics,* Sixth Ed., 1980, MacMillan Publ. Co., Inc., New York, pp. 1–2.

R. G. Douglas, Jr., "Antimicrobial Agnets," Ch. 51 in *Goodman and Gilman's The Pharmacological Basis of Therapeutics,* Eighth Ed., 1990, Pergamon Press, Inc., New York, pp. 1182–1201.

Yarchoan et al., "Correlations between the In vitro and In vivo Activity of Anti–HIV Agents: Implications for Future Drug Development," *J. Enzyme Inhibtion,* 6, 99–111 (1992).

Spectro et al., "Human Immunodeficiency Virus Inhibition Is Prolonged by 3'–Azido–3'–Deoxythymidine Alternating with 2', 3'–Dideoxycytidien Compared with 3–40–Azido–3'–Deoxythymidine Alone," *Antimicrobial Agents and Chemotherapy,* 33(6), 920–923 (1989).

Doulerice et al., "Inhibition by AZT of HIV–1 Replication in Acutely Infected U–937 Cells," *J. Leukocyte Biol.,* 47, 498–505 (1990).

Fridland et al., "Relationships of Deoxynucleotide Changes to Inhibition of DNA Synthesis Induced by the Antiretroviral Agent 3'–Azido–3'–deoxythymidine and Release of its Monphosphate by Human Lymphoid Cells (CCRF–CEM)," *Molecular Pharmacology,* 37, 665–670 (1990).

Mansuri et al, "Comparison of In Vitro Biological Properties and Mouse Toxicities of Three Thymidine Analogs Active Against Human Immunodeficiency Virus," *Antimicrobial Agents and Chemotherapy,* 34(4), 637–641 (1990).

Volsky et al., "Evaluation of Multiple Parameters of HIV–1 Replication Cycle in Testing of AIDS Drugs In Vitro," *Antiviral Research,* 17, 335–347 (1992).

Lambert et al., "Synergistic Drug Interactions of an HIV–1 Protease Inhibitor with AZT in Different In Vitro Models of HIV–1 Infection," *Antiviral Research,* 21, 327–342 (1993).

Panneer et al., "Inhibition of HIV–1 Replication in H9 Cells by Nystatin–A Compared with Other Antiviral Agents," *AIDS Res. Human Retroviruses,* 9(5), 475–481 (1993).

Spinolo et al., "Toxicity of Human p53 Antisense Oligonucleotide Infusions in *Rhesus macacca*," *Proc. Ann. Meeting Am. Assoc. Cancer Res.,* 33, Abstract No. 3125 (1992).

Sarmiento et al., "In vivo Toxicological Effects of rel A Antisense Phosphorothioates in CD–1 Mice," *Antisense Research and Development,* 4, 99–107 (1994).

Iversen et al., "Pharmacokinetics of an Antisense Phosphorothioate Oligodeoxynucleotide Against rev from Human Immunodeficiency Virus Type 1 in Adult Male Rat Following Single Injections and Continuous Infusion," *Antisense Research and Development,* 4, 43–52 (1994).

In vivo Studies with Phosphorothioate Oligonucleotides: Pharmacokinetics Prologue, *Anticancer Drug Des.,* 6, 531–538 (1991).

S. T. Crooke, "Therapeutic Applications of Oligonucleotides," *Ann. Rev. Pharmacol. Toxicol.,* 32, 329–376 (1992).

Chubb et al., "Human Therapeutics Based on Triple Helix Technology," *TIBTECH,* 10(4), 132–136 (1992).

Agrawal et al., "Antisense Oligonucleotides: Gene Regulation and Chemotherapy of AIDS," *Advanced Drug Delivery Reviews,* 6, 251–270 (1991).

Gymer, *Chemistry: An Ecological Appproach,* Harper & Row, Publishers, New York, NY, 1973, pp. 267–271.

5'
GGGUCUCUCUGGUUAGACCAGAUCUGAGCCUGGGAGCUCUCUGGCUAACUAGGGAACCC
3'

Fig. 1A

```
         C       A     UCU    CU
5'-GGGU  UCUCUGGUUAG  CCAGA  GAGC    G
3'-CCCA  AGGGAUCAAUC_ GGUCU_ _CUCG   G
                                    AG
```

2'-O-ALKYLATED OLIGORIBONUCLEOTIDES AND PHOSPHOROTHIOATE ANALOGS COMPLEMENTARY TO PORTIONS OF THE HIV GENOME

This application is a continuation in part of Ser. No. 518,929, filed May 4, 1990, now abandoned; and Ser. No. PCT/US91/02558, filed Apr. 15, 1991.

INTRODUCTION

This invention relates to the field of therapeutics, particularly the treatment of infections of the human immunodeficiency virus (HIV). It relates to the design, synthesis and application of oligonucleotides which inhibit the activity of HIV.

BACKGROUND OF THE INVENTION

This invention relates to materials and methods for modulating the activity of HIV RNA. The invention generally relates to the field of "antisense" compounds, compounds which are capable of specific hybridization with a nucleotide sequence of an RNA. In accordance with preferred embodiments, this invention is directed to methods for achieving therapeutic treatment of disease and regulating gene activity.

It is well known that most of the bodily states in mammals including infectious disease states, are effected by proteins. Such proteins, either acting directly or through their enzymatic functions, contribute in major proportion to many diseases in animals and man. Classical therapeutics has generally focused upon interactions with such proteins in efforts to moderate their disease causing or disease potentiating functions. Recently, however, attempts have been made to moderate the actual production of such proteins by interactions with molecules that direct their synthesis, intracellular RNA. By interfering with the production of proteins, it has been hoped to effect therapeutic results with maximum effect and minimal side effects. It is the general object of such therapeutic approaches to interfere with or otherwise modulate gene expression leading to undesired protein formation.

One method for inhibiting specific gene expression which has been adopted to some degree is the "antisense" approach, where oligonucleotide analogs complementary to a specific, target, messenger RNA, MRNA sequence are used. A number of workers have reported such attempts. Pertinent reviews include C. A. Stein & J. S. Cohen, *Cancer Research*, vol. 48, pp. 2659–2668 (1988); J. Walder, *Genes & Development*, vol. 2, pp. 502–504 (1988); C. J. Marcus-Sekura, *Anal. Biochemistry*, vol. 172, 289–295 (1988); G. Zon, *Journal of Protein Chemistry*, vol. 6, pp-131–145 (1987); G. Zon, *Pharmaceutical Research*, vol. 5, pp. 539–549 (1988); A. R. Van der Krol, J. N. Mol, & A. R. Stuitje, *BioTechniques*, vol. 6, pp. 958–973 (1988) and D. S. Loose-Mitchell, *TIPS*, vol. 9, pp. 45–47 (1988). Each of the foregoing provide background concerning general antisense theory and prior techniques.

Prior attempts to inhibit HIV by various antisense approaches have been made by a number of researchers. Zamecnik and coworkers have used phosphodiester oligonucleotides targeted to the reverse transcriptase primer site and to splice donor/acceptor sites, P. C. Zamecnik, J. Goodchild, Y. Taguchi, P. S. Sarin, *Proc. Natl. Acad. Sci. USA* 83, 4143 (1986). Goodchild and coworkers have made phosphodiester compounds targeted to the initiation sites for translation, the cap site, the polyadenylation signal, the 5' repeat region and a site between the gag and pol genes. J. Goodchild, S. Agrawal, M. P. Civeira, P. S. Sarin, D. Sun, P. C. Zamecnik, *Proc. Natl. Acad. Sci. U.S.A.* 85, 5507 (1988). In the Goodchild study, the greatest activity was achieved by targeting the polyadenylation signal. Agrawal and coworkers have extended the studies of Goodchild by using chemically modified oligonucleotide analogs which were also targeted to the cap and splice donor/acceptor sites. S. Agrawal, J. Goodchild, M. P. Civeira, A. H. Thornton, P. S. Sarin, P. C. Zamecnik, *Proc. Nat'l. Acad. Sci. USA* 85, 7079 (1988). A portion of one of these overlapped a portion of the HIV TAR region but was not found to have exemplary effect. Neither was this oligonucleotide analog designed to interfere with the HIV TAR region. Agrawal and coworkers have used oligonucleotide analogs targeted to the splice donor/acceptor site to inhibit HIV infection in early infected and chronically infected cells. S. Agrawal, T. Ikeuchi, D. Sun, P. S. Sarin, A. Konopka, J. Maizel, *Proc. Natl. Acad. Sci. U.S.A.* 86, 7790 (1989).

Stropp et al. (European Patent Application No. 90103541.8) disclose chemically modified antisense oligonucleotides for inhibiting TAR and the synthesis of the tat protein from HIV-1 and the use of these oligonucleotides in drugs for the treatment of HIV infections. The oligonucleotides and oligonucleosides are derivatives of normal deoxyribonucleic acid oligomers substituted especially at the phosphorus diester bonds and also at the 3' and 5' termini so that they are resistant to nuclease decomposition and have better permeation or hybridization properties. Stropp et al. found that the antisense oligonucleotides having specific sequences showed significantly greater inhibitory activity than prior art oligonucleotides. It was also found that normal deoxyribonucleic acid oligonucleotides were almost completely decomposed in cell culture tests in 2–3 hours. The chemically modified oligonucleotides used by Stropp et al. (phosphorothioates and methyl phosphonates) showed high nuclease resistance, as compared to the oligonucleotides of Goodchild et al. (1988). Stropp et al. disclose antisense oligonucleotides against the following TAR and leader sequences: nucleotides 21-53, 74-161, 202-279 and the second and third exon of the tat gene, nucleotides 5368-5403, 5421-5548, 5583-5617, and nucleotides 7967-8366, 8385-9183 of the HIV-1 genome. In the tests performed, it was found that these oligonucleotides inhibited protein synthesis in the 5' untranslated region, the 3' end of the tat mRNA, and within the tat mRNA. Phosphorothioate oligonucleotides which hybridize in the loop region of TAR MRNA were found to be very effective. Comparative studies with respect to the number of nucleotide monomers showed that effective translation inhibition was achieved with 10-18-mer oligonucleotides. Replacement of one or more bases with other partial structures (e.g., hypoxanthine or other purines, pyrimidines) did not impair hybridization.

Shibahara et al. (European Patent Application No. 89303700.2) disclose 2'-0-methylribo oligonucleotide analogs, phosphorothioate 2-O-methylribo oligonucleotide analogs, and oligonucleotide derivatives complementary to the HIV virus mRNA splice site, to the primer-tRNA binding site, to the region upstream from the gag gene initiation codon, to a region internal to the gag gene, and to nucleotides 19-38 of the TAR element.

Sarin and coworkers have also used chemically modified oligonucleotide analogs targeted to the cap and splice donor/acceptor sites. P. S. Sarin, S. Agrawal, M. P. Civeira, J. Goodchild, T. Ikeuchi, P. C. Zamecnik, *Proc. Natl. Acad. Sci. U.S.A.* 85, 7448 (1988). Zaia and coworkers have also used an oligonucleotide analog targeted to a splice acceptor site to inhibit HIV. J. A. Zaia, J. J. Rossi, G. J. Murakawa, P. A. Spallone, D. A. Stephens, B. E. Kaplan, *J. Virol.* 62, 3914 (1988). Matsukura and coworkers have synthesized oligonucleotide analogs targeted to the initiation of translation of the rev gene mRNA. M. Matsukura, K. Shinozuka, G. Zon, et al, *Proc. Natl. Acad. Sci. USA* 84, 7706 (1987); R. L. Letsinger, G. R. Zhang, D. K. Sun, T. Ikeuchi, P. S. Sarin, *Proc. Natl. Acad. Sci. U.S.A.* 86, 6553 (1989). Mori and coworkers have used a different oligonucleotide analog targeted to the same region as Matsukura. K. Mori, C. Boiziau, C. Cazenave, et al., *Nucleic Acids Res.* 17, 8207 (1989). Shibahara and coworkers have used oligonucleotide analogs targeted to a splice acceptor site as well as the reverse transcriptase primer binding site. S. Shibahara, S. Mukai, H. Morisawa, H. Nakashima, S. Kobayashi, N. Yamamoto, *Nucl. Acids Res.* 17, 239 (1989). Letsinger and coworkers have synthesized and tested oligonucleotide analogs with conjugated cholesterol targeted to a splice site. K. Mori, C. Boiziau, C. Cazenave, et al., *Nucleic Acids Res.* 17, 8207 (1989). Stevenson and Iversen have conjugated polylysine to oligonucleotide analogs targeted to the splice donor and the 5'-end of the first exon of the tat gene. M. Stevenson, P.L. Iversen, *J. Gen. Virol.* 70, 2673 (1989).

These prior attempts at targeting HIV have largely focused on the nature of the chemical modification used in the oligonucleotide. Although each of the above publications have reported some degree of success in inhibiting some function of the virus, a general therapeutic scheme to target HIV and other retroviruses has not been found. Accordingly, there has been and continues to be a long-felt need for the design of oligonucleotides which are capable of effective, therapeutic antisense use.

This long-felt need has not been satisfied by prior work in the field of antisense oligonucleotide therapy for HIV and other retroviruses and viruses. Others have failed to identify target sites in which antisense oligonucleotides s are therapeutically effective at reasonable rates of application.

OBJECTS OF THE INVENTION

It is a principal object of the invention to provide therapies for human diseases, particularly the human immunodeficiency virus.

It is a further object of the invention to provide molecules, especially oligonucleotides which perturb the structure of mRNA.

Yet another object of this invention is to modulate gene expression in cells.

A further object is to interfere with the secondary structure of RNAs through interaction of those structures with oligonucleotides.

Another object is to effect such interference through formation of perturbed RNA secondary structures.

Another object is to effect such interference through formation of nucleotide triplexes.

These and other objects of this invention will become apparent from a review of the instant specification.

SUMMARY OF THE INVENTION

A new paradigm for targeting antisense oligonucleotides to HIV and other retroviruses, viruses and other infectious agents has now been discovered. Prior attempts at antisense targeting to HIV have been focused on inhibition of the synthesis of some particular viral protein thought to be essential to the success of the infection. In the present invention, the same goal (inhibition of viral gene expression) is achieved, but greater, therapeutically significant activity is obtained by targeting particular sites on the HIV or other retrovirus RNA. In the present invention, target RNA structures which have important biological function have been found to be the key target sites. They are interfered with at the level of those structures. It has been determined that targeting these RNA structures is a key to effective antisense therapy with oligonucleotides.

In accordance with the present invention, methods of modulating the expression of genes are provided. These comprise selecting or identifying a portion of RNA coded by the gene which has subportions forming a secondary structure. The RNA, or cells containing it, is then contacted with an oligonucleotide which can bind with at least one of the subportions of the RNA. It is preferred that the oligonucleotide be designed so as to be capable of disrupting the secondary structure of the RNA to effect the inhibition of expression of a gene. The gene is generally one which is believed to give rise to a disease state in an organism and is typically a virus or retrovirus although other infectious organisms can be so attacked.

It is preferred that the oligonucleotide be capable of binding with at least about six subunits of the RNA subportion. It is more preferred that from eight to fifty units be capable of being bound, with from about 10 to about 20 subunits being even more preferred.

In accordance with preferred embodiments, the oligonucleotide is capable of forming a duplex structure with the subportion of RNA. Alternatively, and in accordance with certain preferred embodiments, the oligonucleotide can form a triplex structure with the selected portion of RNA. While the mechanism of the interaction is not known with certainty, it is possible that it may effect modulation of gene expression through a number of ways. In accordance with preferred embodiments, the RNA portion which is interfered with comprises at least a part of the TAR element of HIV.

The oligonucleotides in accordance with this invention are themselves believed to be novel. Thus, oligonucleotides which are capable of interacting with subportions of RNA which are capable of forming secondary structures or triplex structures are comprehended. It is also intended that methods of treating animals suspected of having a disease characterized by expression of a gene coding for RNA having a secondary structure may also be provided. Thus, animals suspected of having the disease are contacted with oligonucleotides which can bind with the secondary structure of the RNA, or forming a triplex structure with the selected portion of mRNA, implicated in the disease process. In particular, the present invention is believed to be effective in the treatment of HIV infections in mammals, especially man. Thus, oligonucleotides designed to interact with a selected element of HIV are administered to animals, especially humans suspected of being infected with human immunodeficiency virus.

BRIEF DESCRIPTION OF THE DRAWINGS

FIG. 1A depicts the linear HIV-1 TAR element sequence. Underlined portions connote predicted loops and bulges when the RNA is folded into a hairpin structure. FIG. 1B depicts a computer-predicted secondary structure or the HIV-1 TAR element.

DETAILED DESCRIPTION OF PREFERRED EMBODIMENTS

Figure 2:
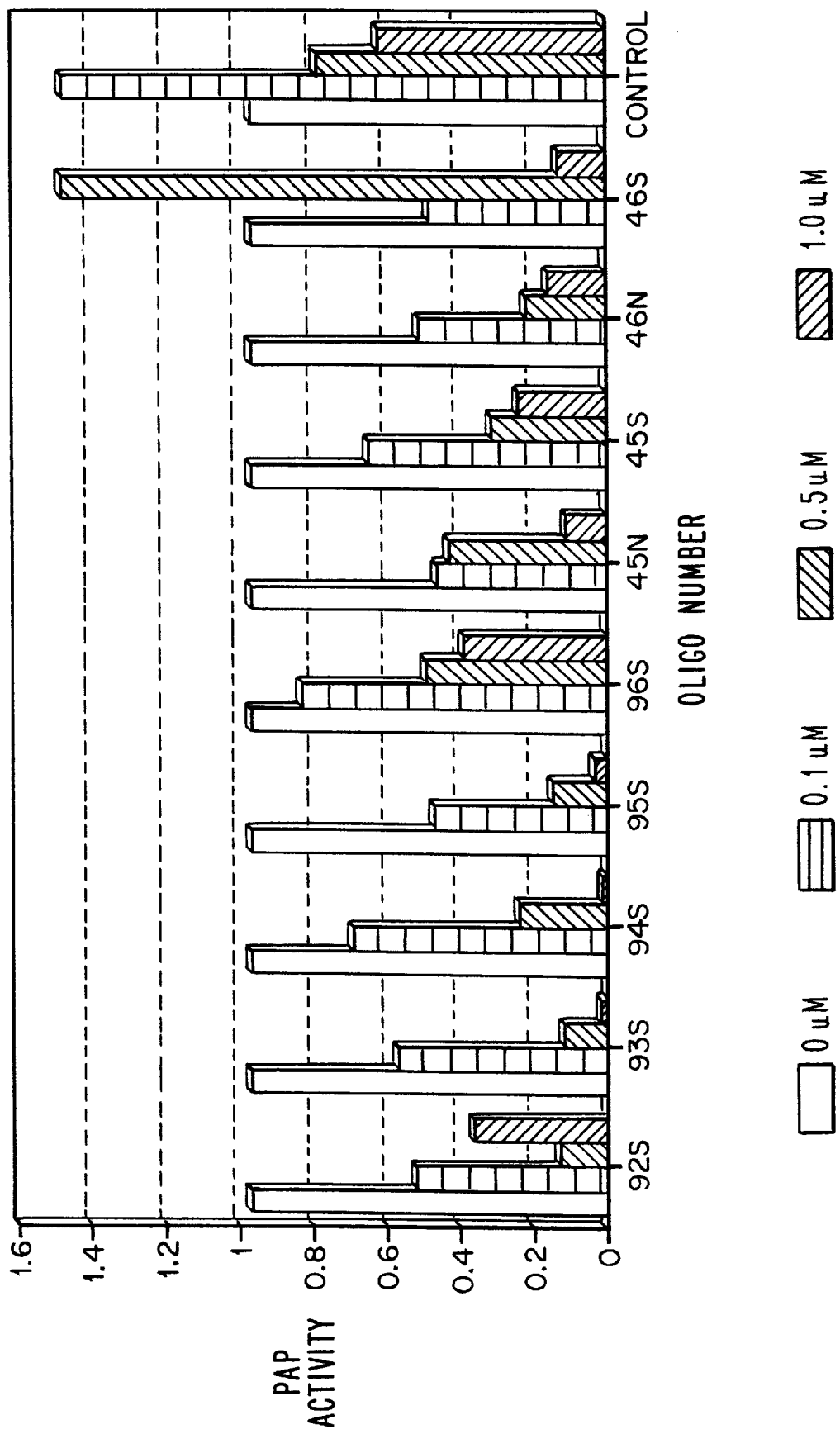
FIG. 2 depicts the activity of a series of oligonucleotides in a cell culture assay for TAR/tat transactivation.

The biological function of RNA is mediated by its structure. Messenger RNA (mRNA) is generally thought of as a linear molecule which contains the information for directing protein synthesis within the sequence of ribonucleotides. Recently, studies have revealed a number of secondary and tertiary structures in mRNA which are important for its function. I. Tinoco, Jr. P. W. Davis, C. C. Hardin, J. D. Puglisi, G. T. Walker, *Cold Spring Harb. Symp. Quant. Biol.* 52, 135 (1987). Secondary structure elements in RNA are formed largely by Watson-Crick type interactions between different regions of the same RNA molecule. Important secondary structural elements include intramolecular double stranded regions, hairpin loops, bulges in duplex RNA and internal loops. Tertiary or triplex structural elements are formed when secondary structural elements come in contact with each other or with single stranded regions to produce a more complex three dimensional structure.

Very little is known about the precise three dimensional structure of RNA. However, there have recently been a number of research efforts which have shown that RNA structures, including single stranded, secondary and tertiary structures, have important biological functions beyond simply encoding the information to make proteins in linear sequences. Some of these correlations have been discussed in the following publications: I. Tinoco, Jr., P. W. Davis, C. C. Hardin, J. D. Puglisi, G. T. Walker, *Cold Spring Harb. Symp. Quant. Biol.* 52, 135 (1987); O. Resnekov, M. Kessler, Y. Aloni, *J. Biol. Chem.* 264, 9953 (1989); C. Tuerk, P. Gauss, C. Thermes, et al., *Proc. Natl. Acad. Sci. U.S.A.* 85, 1364 (1988); and D. E. Larson, B. H. Sells, *Mol. Cell. Biochem.* 74, 5 (1987). Despite the fact that there is little precise structural information on RNA, a number of researchers have measured the binding energies of a large number of RNA duplex structures and have derived a set of rules which can be used to predict the secondary structure of RNA. J. A. Jaeger, D. H. Turner, M. Zuker, *Proc. Natl. Acad. Sci. USA* 86, 7706 (1989); D. H. Turner, N. Sugimoto, *Annu. Rev. Biophys. Biophys. Chem.* 17, 167 (1988). In conjunction with experimental data, these rules are useful in identification of RNA structural elements with important biological function.

It has been discovered to be possible to regulate the activity of RNA in cells by introducing oligonucleotides which perturb or interfere with the secondary structure of natural RNAs. The oligonucleotides interfere with the normal interaction between the RNA and the factors that bind to it. This method can be used to treat diseases, particularly HIV and other retroviruses. In accordance with the present invention, compositions which bind to biological RNA molecules with significant structural features of biological importance are provided. The present invention employs oligonucleotides which bind to these structures.

In the context of this invention, the term "oligonucleotide" refers to a polynucleotide formed from naturally occurring bases and pentofuranosyl groups joined by native phosphodiester bonds. This term effectively refers to naturally occurring species or synthetic species formed from naturally occurring subunits or their close homologs. The term "oligonucleotide" may also refer to moieties which function similarly to naturally occurring oligonucleotides but which have non-naturally occurring portions. Thus, oligonucleotides may have altered sugar moieties or intersugar linkages. Exemplary among these are the phosphorothioate and other sulfur-containing species which are known for use in the art. In accordance with some preferred embodiments, at least some of the phosphodiester bonds of the oligonucleotide have been substituted with a structure which functions to enhance the ability of the compositions to penetrate into the region of cells where the RNA or DNA whose activity to be modulated is located. It is preferred that such substitutions comprise phosphorothioate bonds, methyl phosphonate bonds, or short chain alkyl or cycloalkyl structures. In accordance with other preferred embodiments, the phosphodiester bonds are substituted with other structures which are, at once, substantially non-ionic and non-chiral, or with structures which are chiral and enantiomerically specific. Persons of ordinary skill in the art will be able to select other linkages for use in practice of the invention.

Oligonucleotides may also include species which include at least some modified base forms. Thus, purines and pyrimidines other than those normally found in nature may be so employed. Similarly, modifications on the pentofuranosyl portion of the nucleotide subunits may also be effected, as long as the essential tenets of this invention are adhered to. Examples of such modifications are 2'-O-alkyl- and 2'-halogen-substituted nucleotides. Some specific examples of modifications at the 2' position of sugar moieties which are useful in the present invention are OH, SH, $SCH_3$, F, $OCH_3$, OCN, $O(CH_2)_n NH_2$ or $O(CH_2)n CH_3$ where n is from 1 to about 10, and other substituents having similar properties.

Such oligonucleotides are best described as being functionally interchangeable with natural oligonucleotides (or synthesized oligonucleotides along natural lines), but which have one or more differences from natural structure. All such oligonucleotides are comprehended by this invention so long as they function effectively to hybridize with TAR RNA. The oligonucleotides in accordance with this invention preferably comprise from about 5 to about 50 nucleic acid base units. It is more preferred that such oligonucleotides comprise from about 8 to 25 nucleic acid base units, and still more preferred to have from about 12 to 25 nucleic acid base units. As will be appreciated, a nucleic acid base unit is a base-sugar combination suitably bound to adjacent nucleic acid base unit through phosphodiester or other bonds.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed, however the actual synthesis of the oligonucleotides are well within the talents of the routineer. It is also well known to use similar techniques to prepare other oligonucleotides such as the phosphorothioates and alkylated derivatives.

The oligonucleotides of this invention can be used in diagnostics, therapeutics and as research reagents and kits.

For therapeutic use, the oligonucleotide is administered to an animal, especially a human, such as are suffering from a virus or retrovirus infection such as AIDS.

Oligonucleotides may be formulated in a pharmaceutical composition, which may include carriers, thickeners, diluents, buffers, preservatives, surface active agents and the like in addition to the oligonucleotide. Pharmaceutical compositions may also include one or more active ingredients such as antimicrobial agents, antiinflammatory agents, anesthetics, and the like in addition to oligonucleotide.

The pharmaceutical composition may be administered in a number of ways depending on whether local or systemic treatment is desired, and on the area to be treated. Administration may be topically (including opthalmically, vaginally, rectally, intranasally), orally, by inhalation, or parenterally, for example by intravenous drip, subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

It is generally preferred to apply the therapeutic agent in accordance with this invention internally such as orally, intravenously or intramuscularly. Other forms of administration, such as transdermally, topically or intralesionally may also be useful. Use of the oligonucleotides of this invention in prophylaxis is also likely to be useful. Use of pharmacologically acceptable carriers is also preferred for some embodiments. In accordance with the present invention, the oligonucleotides which are useful in its performance are best described by the RNA whose secondary structure is to interfered with. Thus, it will be understood by persons of ordinary skill in the art that the oligonucleotides provided by this invention are those which are capable of binding with RNA having a secondary structure bearing a causal or mediative relationship to a diseased state. All such oligonucleotides are comprehended by this invention so long as they bind the target RNA structure at or adjacent to a secondary structure thereof.

A number of RNA secondary structures have recently been identified for which application of this invention will likely provide therapeutic utility. Others will also be useful as well. Some of these include the HIV TAR structures; S. Feng, E. C. Holland, Nature 334, 165 (1988), including the stem loops at nucleotide 1-59, and 60-104 according to the nucleotide sequence as described by Ratner L. Ratner L.; W. Haseltine, R. Patarca, K. J. Livak, B. Starcich, S. F. Josephs, *Nature* 313, 277 (1985); the boundary between the EGP/OMP regions of HIV, S. Le, J. Chen, M. J. Braun, M. A. Gonda, J. V. Maizel, *Nucl. Acids Res.* 16, 5153 (1988); the boundary between the TMP/env genes of HIV, S. Le, J. Chen, M. J. Braun, M. A. Gonda, J. V. Maizel, *Nucl. Acids Res.* 16, 5153 (1988); the HIV CAR structure, E. T. Dayton, D. M. Powell, A. I. Dayton, Science 246, 1625 (1989); the stem loop structure at the junction between the HIV qap and pol genes (nucleotides 1629-1674); the HIV CRS element; and the human iron responsive element (IRE) J. L. Casey, M. W. Hentze, D. M. Koeller, et al, *Science* 240, 924 (1988).

In addition, there are regions of RNA which are primarily thought of as single stranded areas which have been identified as sites for protein binding. For example, the sequence 5'-AUUUA-3' has been identified as a signal for a protein to bind which leads to degradation of RNA. J. S. Malter, *Science* 246, 664 (1989). The structure of this region in not known. However, that does not preclude the practice of this invention with this sequence. Additional RNA elements, with as yet unknown structures, can also be the subject of this invention.

It is not absolutely necessary to know the actual RNA structure in order to practice this invention, it is only necessary to know that a specific RNA sequence is recognized by an RNA binding element and that this interaction has important biological consequences. In this regard, the viral RNA sequences and structures which are recognized by the structural proteins of retroviruses for virion formation may be the subject of this invention as may many others. It is not intended that application of this invention be limited to presently known structures. Binding to any RNA structure which has an important biological function falls within the spirit and scope of this invention.

This disclosure provides several methods to interfere with the natural function of an RNA structural element and others will be apparent to persons skilled in the art. By using the rules of Watson-Crick hybridization and free energy predictions for hybridization of oligonucleotides designed to be complementary to RNA which comprises secondary structures it has now been found that the oligonucleotides will compete with internal RNA structures by forming stable heteroduplexes. The energy barriers to heteroduplex formation are overcome by designing oligonucleotides to form a more stable heteroduplex than the internal RNA structure on the target RNA.

Kinetic considerations for strand invasion of an existing RNA duplex also enter into the oligonucleotide design. It is possible to disrupt an existing RNA secondary structure with an invading strand by designing the invading strand to have at least three, and preferably more bases complementary to regions to the target RNA which are not involved in base pairing. This provides a kinetic "foothold" for the invading strand to initiate the process of heteroduplex formation.

It is also disclosed that duplex RNA structure can be perturbed by binding to it by triple strand formation. In contrast to heteroduplex formation, where the RNA secondary structure is broken by an invading strand, triple strand formation generally preserves the existing RNA duplex hydrogen bonding pattern, but binds in a helical groove with additional hydrogen bonds. Triple strand formation is a phenomenon which has been known in a limited sense for some time. General reviews which describe triple strand formation with duplex DNA include; J. C Hanvey, M. Shimizu, R. D. Wells, *Proc. Natl. Acad. Sci. USA* 85, 6292 (1988); and S. Arnott, E. Selsing, *J. Mol. Biol.* 88, 509 (1974). Triple strand formation with RNA homopolymers has been previously described in S. L. Broitman, D. D. Im, J. R. *Fresco, Proc. Natl. Acad. Sci. USA* 84, 5120 (1987). It has not, however, previously been disclosed to inhibit the function of RNA by binding to duplex regions with oligonucleotides or by triple strand formation. It is now believed, however, that binding to regions of RNA secondary structure, such as in the stem regions of stem-loops, will perturb the interactions between the natural RNA and the factors which bind to it, thus modulating gene expression.

In accordance with the present invention, it will be understood that the term "to bind" as it refers to the interaction between an oligonucleotide and an RNA portion or subportion may have any of several, related meanings. Thus, the present invention comprehends binding of an oligonucleotide with at least one of the subportions forming a secondary structure of an RNA portion comprising them. It will be understood that the oligonucleotide will bind with at least one of the subportions of the RNA portion in a Watson-Crick fashion so as to form, locally, a heteroduplex between the RNA subportion and the oligonucleotide. This heteroduplex formation is believed to result in alteration of the secondary structure of the RNA portion. The exact mechanism and the result of this effect is not known with certainty, yet it is believed that the normal secondary structure of the RNA portion is gradually replaced by the binding of the oligonucleotide with one or more of the subportions of the RNA portion. Since the electronic and steric factors which attend the new heteroduplex are different from those of the naturally occurring RNA portion, the effectiveness and nature of the function to generate protein from the RNA is interfered with. The resulting formation of defective or missing protein manifests itself overall as a modulation in the expression of the gene coding for the RNA.

The present invention also comprehends the formation of triplexes with RNA portions having secondary structures. Once again, the precise nature of such triplexes is not fully understood; however it is believed that suitably constructed oligonucleotides can so interact with portions of RNA having a secondary structure in some circumstances. The resulting triplex formation is believed to grossly interfere with translation of protein from the RNA thus leading to modulation of expression of the gene from which the RNA derives.

In accordance with the invention it is not necessary that the interaction of oligonucleotide with the RNA portion or subportion—the binding of the two—result in either non-formation or malformation of protein. It may be in some circumstances that interruption of some control or other function having a significant role in the gene expression protocol may be an effective means of modulating that expression. One example of this relates to the gag-pol locus in HIV. Thus, it is not necessary that protein translation be stopped or that defective proteins be produced. Rather, through interference of the gag-pol region it is believed possible to interfere with frame-shifting which is believed to lead to the preparation of fusion proteins of significant importance to the HIV organism.

In short, any interaction or binding of oligonucleotide with an RNA having a secondary structure is believed to have the potential for interference with RNA function and, hence, for modulation of the expression of the gene from which the RNA derives. It is likely that persons of ordinary skill in the art will find other means of interfering with RNA secondary structures other than those set forth with specificity herein. All such means are, however, contemplated by the present invention.

While a wide variety of oligonucleotides are believed to be useful in practice of the present invention, it has been found to be preferred to design such oligonucleotides so as to bind with at least about six subunits of a subportion of an RNA portion having a secondary structure. In accordance with other preferred embodiments, oligonucleotides which combine with from about six to about 30 and even more preferably with about 10 to about 20 subunits are preferred. As discussed above, the TAR element of HIV has been found to be an excellent target for employment of the present invention. Accordingly, preparation of oligonucleotide for binding with one or more subportions of the TAR region of HIV are preferred.

Therapeutics are particular objects of the present invention. Thus, presenting oligonucleotides in accordance with the present invention in pharmaceutically acceptable carriers may be highly useful. It is desired to treat animals suspected of having diseases characterized by expression of genes coding for RNA having secondary structures. Thus, animals suspected of having such diseases are contacted with oligonucleotides which are designed to bind with a secondary structure of those RNAs. This is especially true for treatment of the disease AIDS. In such case, it is presently preferred to employ oligonucleotides which are targeted at the TAR. Overall, it is preferred to administer to patients suspected of suffering from the foregoing disease states, effective amounts of oligonucleotide in either native form or suspended in a carrier medium, in amounts and upon treatment schedules which are effective to reduce the symptomology of that disease. It is within the scale of a person's skill in the art to determine optimum dosages and treatment schedules for such treatment regimens.

EXAMPLES

Example 1

The HIV TAR Element

An elaborate set of control elements in the HIV genome determine whether the virus replicates or remains dormant. of the nine genes identified in the HIV genome, only three are from the core and envelope. W. A. Haseltine, F. Wong-Staal, Scientific American, 52 (October, 1988). The other six genes are involved in regulation of the production of viral proteins. Regulatory genes work by encoding a protein that interacts with a responsive element somewhere else on the viral genome. The major regulatory gene responsible for initiating the burst of replication is the tat (trans-activator) gene. The product of the tat gene, tat protein, works by interaction with a short sequence element known as TAR (trans-acting responsive element). The TAR sequence is encoded in the viral long terminal repeats (LTR's), and therefore is included in the MRNA from every HIV gene.

Expression of the tat protein results in increased expression of other HIV genes up to 1,000 fold, including the tat gene itself. Because of this autoregulatory positive feedback, and the fact that the TAR sequence is included in the mRNA from every HIV transcript, an immense amount of viral gene expression is triggered when the tat gene is activated. The interaction between the tat gene and the TAR element is therefore crucial to the life cycle of the HIV, and specific disruption of this interaction is likely to interrupt the propagation of the virus.

The mechanism of trans-activation of TAR-containing genes by the tat protein has recently been studied intensely. Phillip, A. Sharp, Robert, A. Marciniak, Cell, 59:229 (1989). Although much remains to be learned, two important points have become clear; that tat increases the expression of TAR-containing genes by increasing both the amount of viral mRNA and the efficiency of its translation, and that TAR functions as an RNA structure, rather than a DNA structure.

The unusual conclusion that tat increases the transcription of TAR-containing genes, but does so by interacting with the TAR element in RNA was derived from a number of observations. Phillip, A. Sharp, Robert, A. Marciniak, Cell, 59:229 (1989). In order to achieve trans-activation, the TAR element must be located immediately downstream from the site of initiation of transcription. Moreover, TAR is orientation dependent; if inserted in the inverse orientation, it fails to function.

Some of the strongest evidence that tat interacts with TAR as an RNA structure has come from mutagenesis experiments. Efforts to study the TAR element were stimulated by the observation that the tat protein from HIV-1 was capable of trans-activating vectors containing the TAR region of HIV-2, a different strain of virus, even though there is very little primary sequence homology in the TAR region between the two strains. S. Feng, E. C. Holland, *Nature*, 334:165 (1988). However, examination of the TAR sequence from HIV-1 and HIV-2 with computer programs that predict RNA secondary revealed the potential of RNA stem-loop structures, with a single stem-loop in the TAR region of HIV-1 and three stem-loop structures in HIV-2. Although the compositions and lengths of the stems were divergent, all four loops contained the pentanucleotide CUGGG as shown in FIGS. 1A and 1B. Mutagenesis experiments revealed that each of the nucleotides present in the loop are absolutely essential for trans-activation by tat, but that base substitutions in the stem were tolerated to some extent so long as the stem structure was maintained. S. Feng, E. C. Holland, *Nature*, 334:165 (1988).

Further evidence for the TAR structure functioning as RNA was obtained from experiments in which the sequences flanking the stem-loop structure were altered creating competing secondary structures in the RNA that were more stable than the natural TAR stem-loop. B. Berkhout, *Cell*, 59:273 (1989). This was accomplished by introducing additional sequences into the TAR-containing RNA that were antisense to the 5' side of the stem-loop structure. Trans-activation of the modified TAR structure was lost, suggesting that the TAR sequences alone are not sufficient for trans-activation, but that these sequences must fold up in the proper secondary structure to be active. It also suggests that antisense sequences to the TAR stem-loop are capable of disrupting the natural RNA structure.

Direct biochemical evidence for TAR stem-loop structure has also been obtained. The TAR RNA has been enzymatically synthesized in vitro and probed with enzymes which selectively cleave single stranded regions of RNA, but not duplex structures. The results of the enzyme cleavage patterns were consistent with the computer predicted RNA secondary structure. B. Berkhout, *Cell*, 59:273 (1989).

In summary, there is strong and direct evidence from a number of studies that the HIV tat protein is responsible for triggering an enormous amount of viral gene expression, that this occurs by interaction with the TAR sequence which is incorporated into every HIV mRNA transcript, that the HIV TAR sequence functions as an RNA structure and that the correct TAR RNA structure is essential for tat trans-activation.

It has now been discovered that compounds which specifically bind the TAR RNA structure and interfere with tat trans-activation have activity as therapeutic agents for HIV infection. It is intended that all strains of HIV fall within the spirit and scope of this invention. Different strains of HIV may have different TAR sequences which will therefore fold into different structures. This invention can be practiced on alternative strains of HIV by changing the sequence of the oligonucleotide to complement the structure of the alternative strain.

TAR and tat function has been studied by removing the genes from the HIV genome and studying them in cell lines in isolation. Vectors have been constructed to study the interactions between the tat protein and TAR element. The tat gene is expressed under the SV40 promoter. The TAR region is expressed from a separate plasmid fused to an easily assayed reporter gene, the placental alkaline phosphatase gene (PAP). P. Henthorn, P. Zervos, M. Raducha, H. Harris, T. Kadesch, *Proc. Natl. Acad. Sci. USA*, 85:6342 (1988). Enzymatic activity in cell culture models has been shown to be dependent upon both the presence of the essential elements of the TAR region and the presence of the tat protein. P. Sharp, R. Marciniak, *Cell* 59, 229 (1989); S. Feng, E. C. Holland, Nature, 334:165 (1988); Michael, F. Laspia, Andrew, P. Rice, Michael, B. Mathews, *Cell*, 59:283 (1989); J. A. Garcia, D. Harrich, E. Soultanakis, F. Wu, R. Mitsuyasu, R. B. Gaynor, *EMBO J.*, 8:765 (1989); and B. Berkhout, *Cell*, 59:273 (1989). In essence, the vector system reconstitutes the events of tat-mediated TAR trans-activation which occurs in HIV infected cells.

TAT/TAR trans-activation can be conveniently assayed by placing the human placental alkaline phosphatase gene (PAP) under the regulatory control of the HIV-1 LTR sequences, which contain enhancer, promoter, and tar elements. A plasmid containing the HIV-1 LTR, pHIVCAT-0 (S. Feng, E. C. Holland, *Nature*, 334:165 (1988)), contains HIV U3 in its entirety and R up through position +78 (a HindIII site). Digestion of this plasmid with a combination of HindIII and AatII releases the CAT cassette along with the SV40 sequences responsible for the processing of the RNA. A second plasmid, pSV2Apap, contains the PAP cassette with eukaryotic processing signals, under the transcriptional control of an SV40 promoter. P. Henthron, P. Zervos, M. Raducha, H. Harris, T. Kadesch, *Proc. Natl. Acad. Sci. USA*, 85:6342 (1988). The PAP cassette and processing sequences were released from the plasmid by digestion with HindIII and AatII. A new plasmid, pHIVPAP, was created by ligating the HindIII/AatII fragment containing the HIV-1 LTR and vector sequences from pHIVCAT-0, to the HindIII/AatII PAP cassette from pSV2Apap.

To test the activity of oligonucleotides, pcDEBtat and pHIVPAP were co-transfected into HeLa cells by calcium/phosphate precipitation. The effects of oligonucleotides were determined as follows. HeLa cells were split 1:8 into 6-well dishes the day prior to the transfections. For each dish, 1 $\mu$g of PHIVPAP and 12 $\mu$g of pcDEBtat were precipitated in 500 $\mu$l of HBS and 32 $\mu$l of 2.5 M CaCl$_2$. The CaPO$_4$ precipitate was divided evenly between the 6 wells. Oligonucleotides were precipitated in the same manner and added to wells at the concentrations indicated on the figures (the volume is 1.5 ml of media per well). The precipitate was allowed to sit on the cells for 20 minutes, then complete media was added and the cells were incubated for an additional 4 hours. The cells were then shocked with 10% glycerol in HBS. For FIG. 2 only, oligonucleotide was added back to the media following the transfection at a 10 fold higher dose per well. After 48 hours, cells were harvested and protein and PAP assays performed as described by Henthorn et al. P. Henthorn, P. Zervos, M. Raducha, H. Harris, T. Kadesch, *Proc. Natl. Acad. Sci. USA*, 85:6342 (1988) with the following modifications. The cells were harvested in 0.5 ml of TBS, of which 0.1 mls were used for use in the protein assay. The remaining 0.4 mls of cell suspension was pelleted then resuspended in 50 $\mu$l TBS. Endogenous phosphatases were inactivated by heating the cells at 65° C. for 30 minutes. The heat stable human placental alkaline phosphatase activity was assayed by the addition of PNPP (0.5 ml, 5 mM PNPP) to the cell suspension, which was then incubated at 37° C. Activity was determined at 30 minute intervals using 150 $\mu$l aliquots of the reaction mixture and measuring absorbance at 405 nm with a Titertek Multiscan MCC340 ELISA plate reader. The PAP activity was normalized to the total protein in each well as determined by Bio-Rad protein assay, in which ⅕ of the harvested cells in TBS(0.1 $\mu$l) were added to 30 $\mu$l of BioRad Protein Reagent, then incubated for 10 minutes at room temperature, followed by measurement of absorbance at 595 nm using the Titertek plate reader.

Cells were treated with the following oligonucleotides:

| # | Sequence 5'--3' |
|---|---|
| 91 | TCCCAGGC |
| 92 | GTCTAACCAGAGAGACCC |
| 93 | CAGATCTGGTCTAACCAGAGAGACCC |
| 94 | GCTCCCAGGCTCAGATCT |
| 95 | GCCAGAGAGCTCCCAGGCTCAGATCT |
| 96 | GCCAGAGAGCTCCCAGGC |
| 45 | GCTTAAGCAGTGGGTTCCCT |
| 46 | CTTTATTGAGGCTTAAGCAG |

Control oligo CGACTCCGTGCTGGCTCTGA (RANDOM SEQUENCE)

Figure 3:
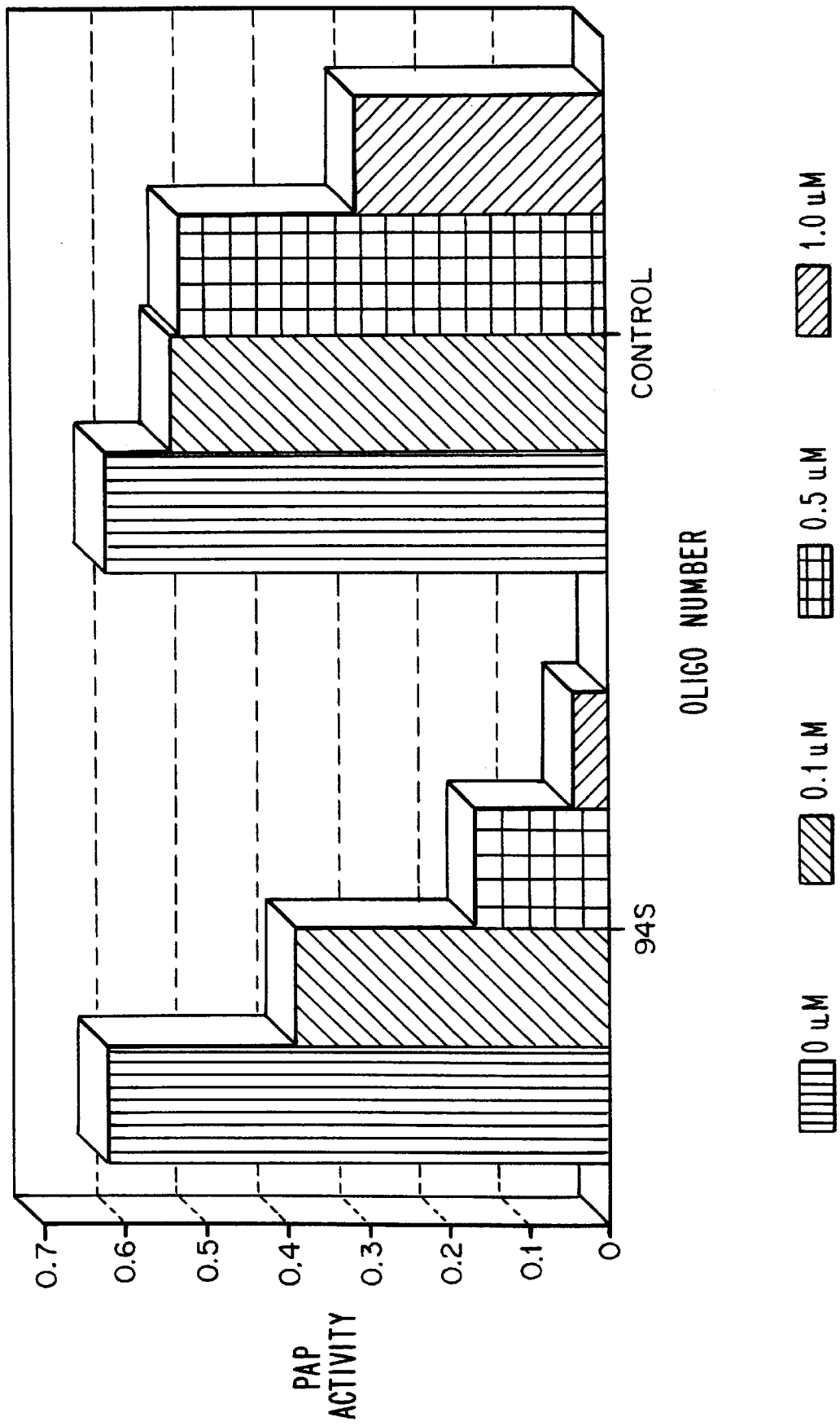
FIG. 3 depicts the activity of the oligonucleotide phosphorothioate 94S in a cell culture assay for TAR/tat transactivation.
Figure 4:
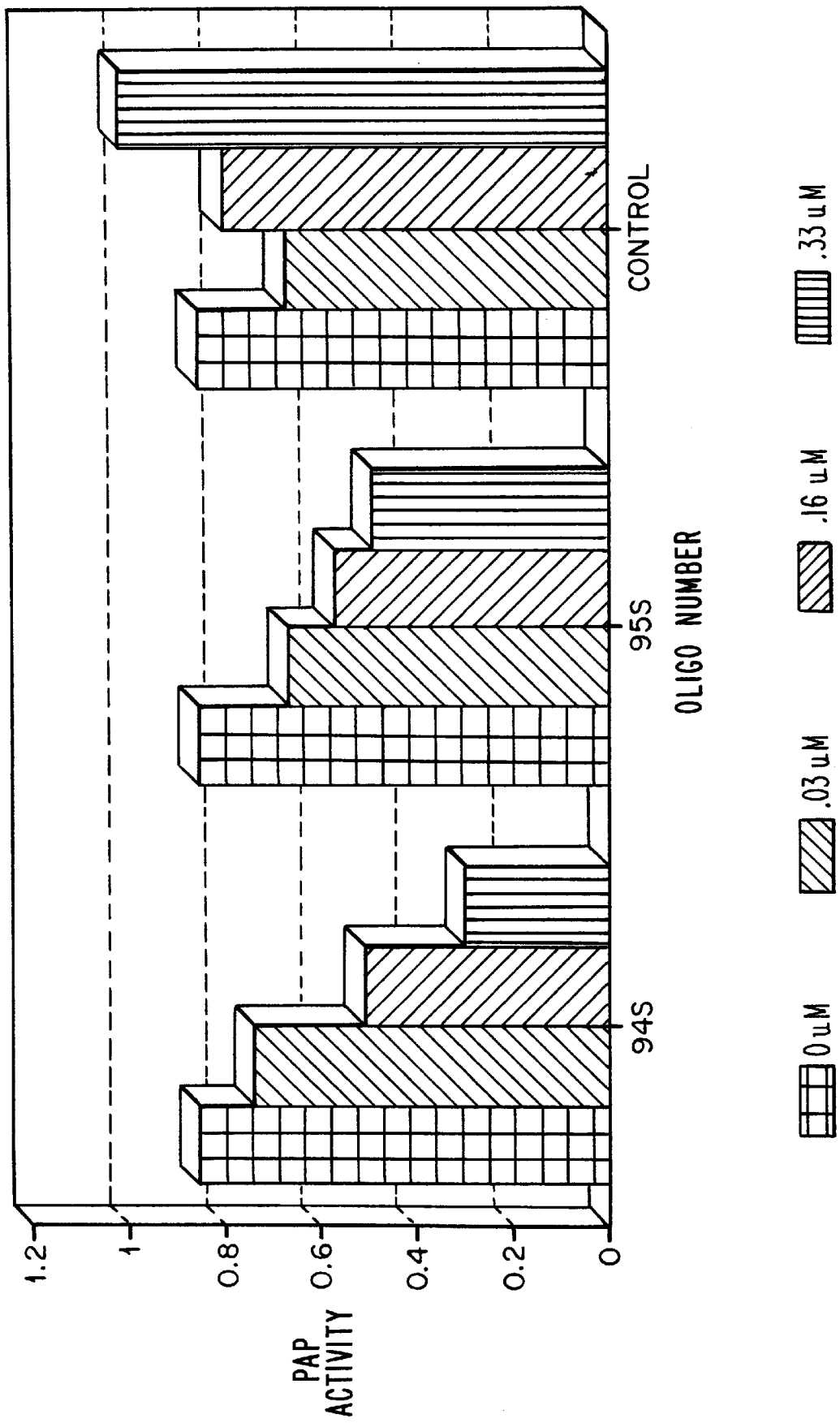
FIG. 4 depicts the activity of the oligonucleotide phosphorothioates 94S and 95S in a cell culture assay for TAR/tat transactivation with a lower dose regimen.

In FIGS. 2–4, the oligonucleotide is numbered, followed by a letter (S or N), where oligonucleotides containing phosphodiester linkages are followed by "N" and oligonucleotides containing all phosphorothioate linkages are followed by an "S". The results shown in FIGS. 2–4 represent three independent experiments.

Example 2

Synthesis of Oligonucleotides: Unmodified DNA oligonucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2 M solution of 3H-1, 2-benzodithiole-3-one 1,1-dioxide in acetonitrile for the stepwise thiation of the phosphite linkages. The thiation cycle wait step was increased to 68 seconds and was followed by the capping step. 2'-O-methyl phosphorothioate oligonucleotides were synthesized using 2'-O-methyl β-cyanoethyldiisopropyl-phosphoramidites (Chemgenes, Needham MA) and the standard cycle for unmodified oligonucleotides, except the wait step after pulse delivery of tetrazole and base was increased to 360 seconds. The 3'-base used to start the synthesis was a 2'-deoxyribonucleotide.

2'-O-alkylated adenosines and corresponding amidites were prepared as disclosed in PCT patent application Serial Number US91/00243, filed Jan. 11, 1991, which is assigned to the same assignee as the instant application, and which is incorporated by reference herein.

After cleavage from the controlled pore glass column (Applied Biosystems) and deblocking in concentrated ammonium hydroxide at 55° C. for 18 hours, the oligonucleotides were purified by precipitation twice out of 0.5 M NaCl with 2.5 volumes ethanol. Analytical gel electrophoresis was accomplished in 20% acrylamide, 8 M urea, 45 mM Tris-borate buffer, pH 7.0. Oligodeoxynucleotides and phosphorothioates were judged from electrophoresis to be greater than 80% full length material.

RNA oligonucleotide synthesis was performed on an ABI model 380B DNA synthesizer. The standard synthesis cycle was modified by increasing the wait step after the pulse delivery of tetrazole to 900 seconds. The bases were deprotected by incubation in methanolic ammonia overnight. Following base deprotections the oligonucleotides were dried in vacuo. The t-butyldimethylsilyl protecting the 2' hydroxyl was removed by incubating the oligonucleotide in 1 M tetrabutylammoniumfluoride in tetrahydrofuran overnight. The RNA oligonucleotides were further purified on $C_{18}$ Sep-Pak cartridges (Waters, Division of Millipore Corp., Milford MA) and ethanol precipitated.

The relative amounts of phosphorothioate and phosphodiester linkages obtained by this synthesis were periodically checked by $^{31}$p NMR spectroscopy. The spectra were obtained at ambient temperature using deuterium oxide or dimethyl sulfoxide-$d_6$ as solvent. Phosphorothioate samples typically contained less than one percent of phosphodiester linkages.

The oligonucleotides made are shown in Table 1:

TABLE 1

| ISIS # | CODE # | LENGTH | SEQUENCE | TARGET | MODIF. | SEQ. ID. NO. |
|---|---|---|---|---|---|---|
| 1308 | 94 | 18 | GCT CCC AGG CTC AGA TCT | TAR | P=S | 1 |
| 1116 |  | 18 | " | TAR | P=O |  |
| 1497 |  | 18 | GCA CCG CTA GCT CCA TGT | random | P=S |  |
| 1485 |  | 18 | " | random | P=O |  |
| 1307 | 95 | 26 | GCC AGA GAG CTC CCA GGC TCA GAT CT | TAR | P=S | 2 |
| 1118 |  | 26 | " | TAR | P=O |  |
| 1720 |  | 26 | TGA CGC AGC AAT TCC AAC TCC GGG GC | random | F=S |  |
| 1716 |  | 26 | " | random | P=O |  |
| 1972 |  | 28 | CCA GAG AGC TCC CAG GCT CAG ATC TGG T | TAR | P=S | 3 |
| 1971 |  | 28 | " | TAR | P=O |  |

Example 3

In Vitro Binding of Oligonucleotides to the TAR Element:

Oligonucleotides hybridizable with the HIV TAR element were synthesized as in Example 2. Binding constants of oligonucleotides to the TAR element were determined by gel shift assay.

Sequences and dissociation constants for these oligonucleotides (given in nM) are shown in Table 2:

TABLE 2

Oligonucleotides Targeted to TAR

| ISIS # NO. | Length | Modification | Sequence | $K_D$ in nM | SEQ. ID. |
|---|---|---|---|---|---|
| 1307 | 26 | P═S | GCC AGA GAG CTC CCA GGC TCA GAT CT | 800 | 4 |
| 1118 | 26 | P═O | " | 1000 | |
| 2250 | 12 | RNA | GAG CUC CCA GGC | 70–80 | 5 |
| 2256 | 12 | DNA | " | none | |
| 2262 | 12 | P═S | " | none | |
| 2523 | 12 | 2'-O—Me | " | 70 | |
| 2273 | 12 | RNA | CCC AGG CUC AGA | 50–70 | 6 |
| 2697 | 12 | 2'-O—Me | " | 30 | |
| 3160 | 17 | RNA | AGA GAG CUC CCA GGC UC | 25 | 7 |
| 3593 | 17 | DNA | " | >>100,000 | |
| 3280 | 17 | 2'-O—Me | " | 18 | |
| 3841 | 17 | 2'-O—Me, P═S cap | " | 20–30 | |
| 3845 | 17 | 2'-O—Me, P═S | " | 200 | |
| 3162 | 17 | RNA | CUC CCA GGC UCA GAU CU | 15 | 8 |
| 3594 | 17 | DNA | " | >100,000 | |
| 3281 | 17 | 2'-O—Me | " | 7 | |
| 3840 | 17 | 2'-O—Me, P═S cap | " | 10 | |
| 3846 | 17 | 2'-O—Me, P═S | " | 150 | |
| 2581 | 17 | RNA | GAG CUC CCA GGC UCA GA | 500 | 9 |

"P═S cap" -- only the 3 P═O linkages at the 3' end are replaced by P═S.
"P═S" indicates all linkages are P═S It can be seen that the 12-nucleotide sequence of oligonucleotides 2250 and 2523 is a subset of the 26-nucleotide sequence (1307 and 1118). While it is generally assumed that binding affinity increases with oligonucleotide length, the data presented here show that the 2'-O-methylated short sequence shows greater than 100-fold tighter binding to TAR than does the phosphorothioate which is more than twice as long.

Example 4
Binding Affinity of 2'-O-alkyl Oligonucleotides to TAR

A series of 2'-O-alkyl-modified oligonucleotides having the same sequence as ISIS 2250 were prepared, in which both of the adenosines (#2, #9) in the sequence were replaced by 2'-O-alkyl-substituted adenosine.

Binding affinities of 2'-O-alkyl-A oligonucleotides to TAR were determined by gel shift in 100 mM Na+ as in Example 2. Results are shown in Table 3.

TABLE 3
Binding affinities of 2'-O-alkyl-A oligonucleotides to TAR (All bases except A are 2'-O-methyl)

TABLE 3

Binding affinities of 2'-O-alkyl-A oligonucleotides to TAR (All bases except A are 2'-O-methyl)

| ISIS # | Substitution on A's | $K_D$ in nM |
|---|---|---|
| 2523 | 2'-O-methyl | 49 |
| 3287 | 2'-deoxy | 45 |
| 2946 | 2'-O-ethyl | 47 |
| 2958 | 2'-O-propyl | 42 |
| 2963 | 2'-O-butyl | 91 |
| 2707 | 2'-O-pentyl | 46 |
| 2991 | 2'-O-nonyl | 59 |
| 2902 | 2'-O-benzyl | 47 |

Figure 5:
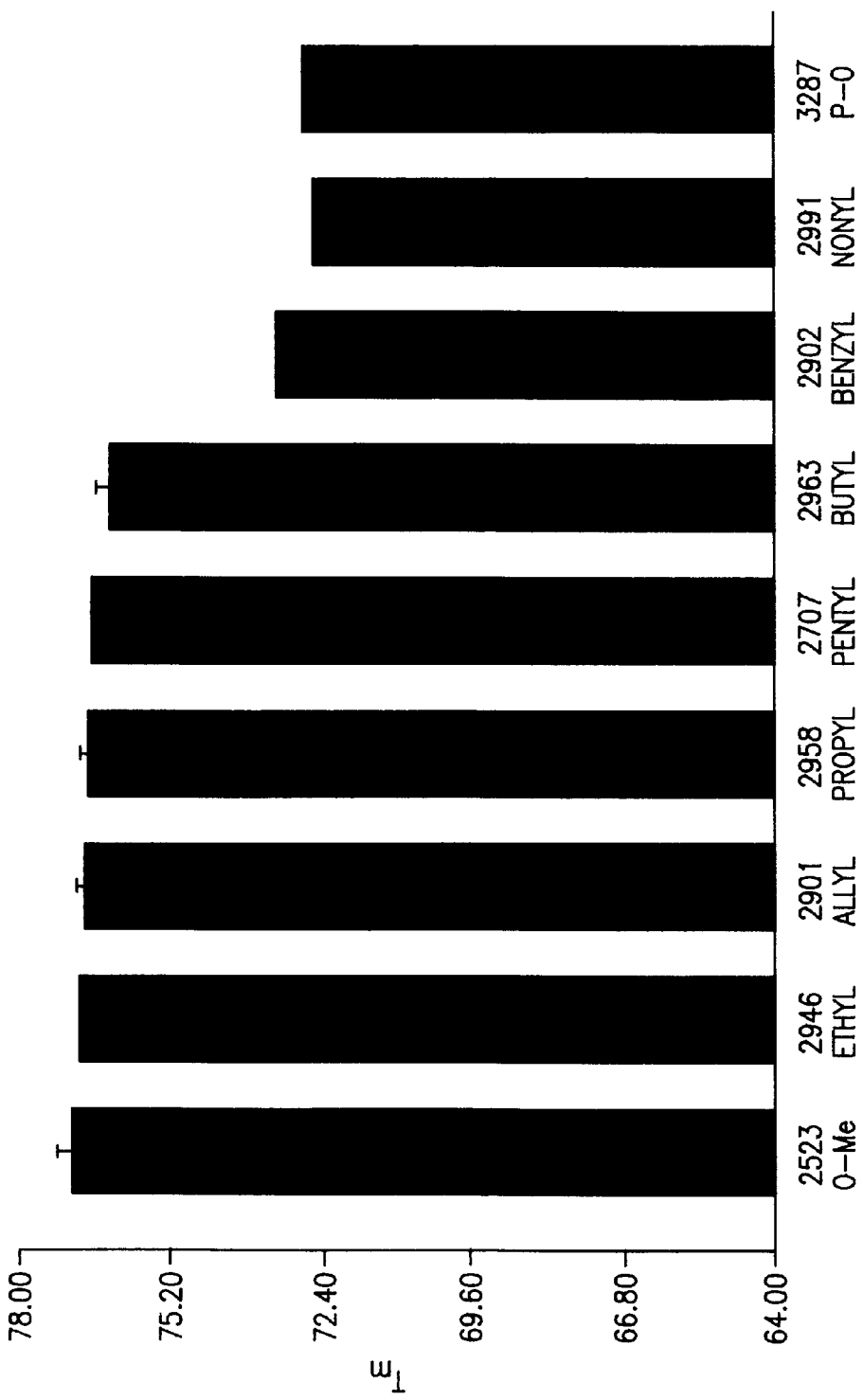
FIG. 5 is a graph showing melting temperatures (Tm) for a series of 2'-O-alkyl-substituted oligonucleotides vs. their RNA complement.

With the exception of 2'-O-butyl, the binding affinities of all the 2'-O-modified oligonucleotides to TAR are very similar. When these oligonucleotides are hybridized to their RNA complements, the Tm remains approximately constant for all but the bulkier alkyl groups (benzyl, nonyl), which have somewhat decreased melting temperatures. It should be noted that the Tm of the phosphodiester oligonucleotide without 2'-substitutions is comparable to the lowest of the 2'-O-alkyl substituted oligonucleotides (FIG. 5).

Figure 6A:
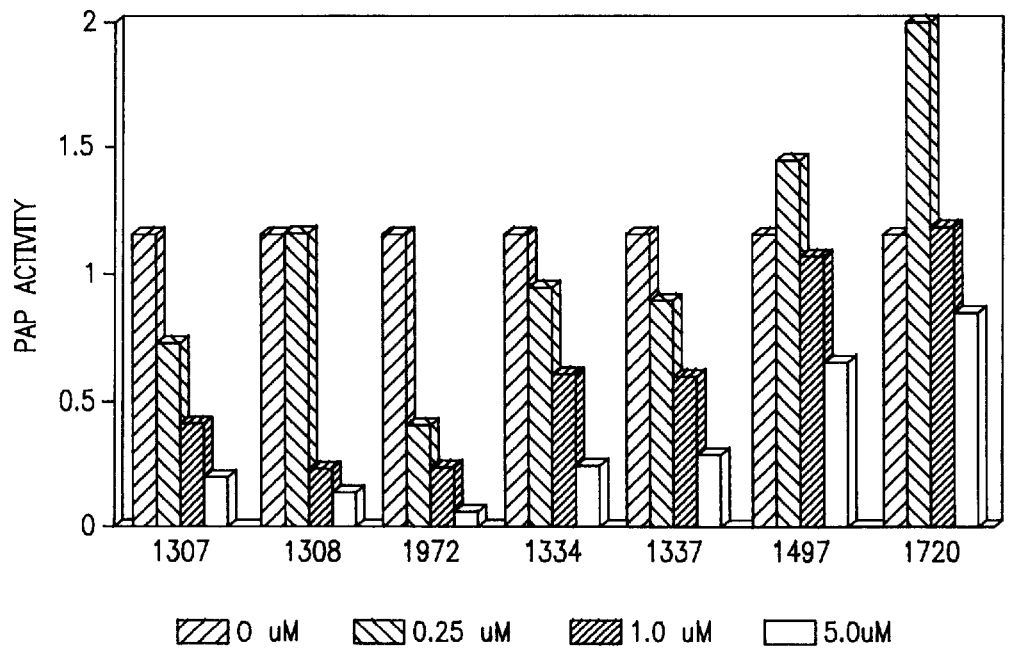
FIG. 6A and 6B are bar graphs showing antisense oligonucleotide inhibition of HIV LTR expression (pHIVpap assay)
Figure 6B:
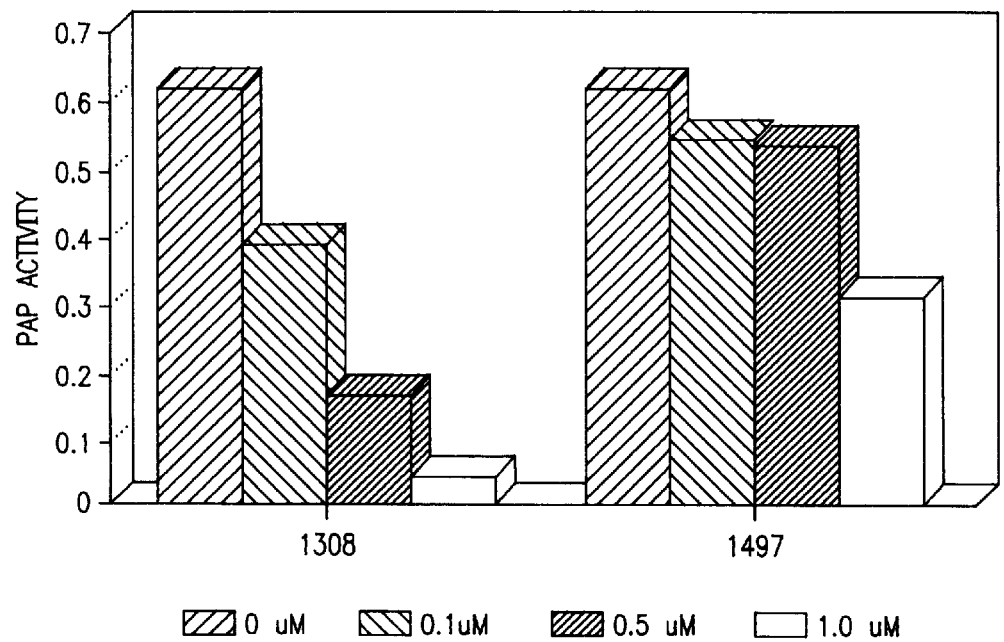

Example 5
Antisense Inhibition of Transactivation:

The TAR-specific oligonucleotides and randomized control oligonucleotides with the same base composition were tested for inhibition of transactivation in a cell culture model using the HIV LTR fused to the human placental alkaline phosphatase gene as described in Example 1. Expression of the reporter gene is strictly dependent upon the presence of tat and, therefore, specific disruption of the TAR/tat interaction is expected to inhibit gene expression. Specific inhibition of HIV LTR gene expression was demonstrated with TAR-specific phosphorothioates (1307, 1308, 1972) relative to matched controls (1497, 1720). This is shown in FIG. 6.

In each case, the phosphodiester versions of the active sequences were ineffective in inhibiting gene expression.

Figure 7:
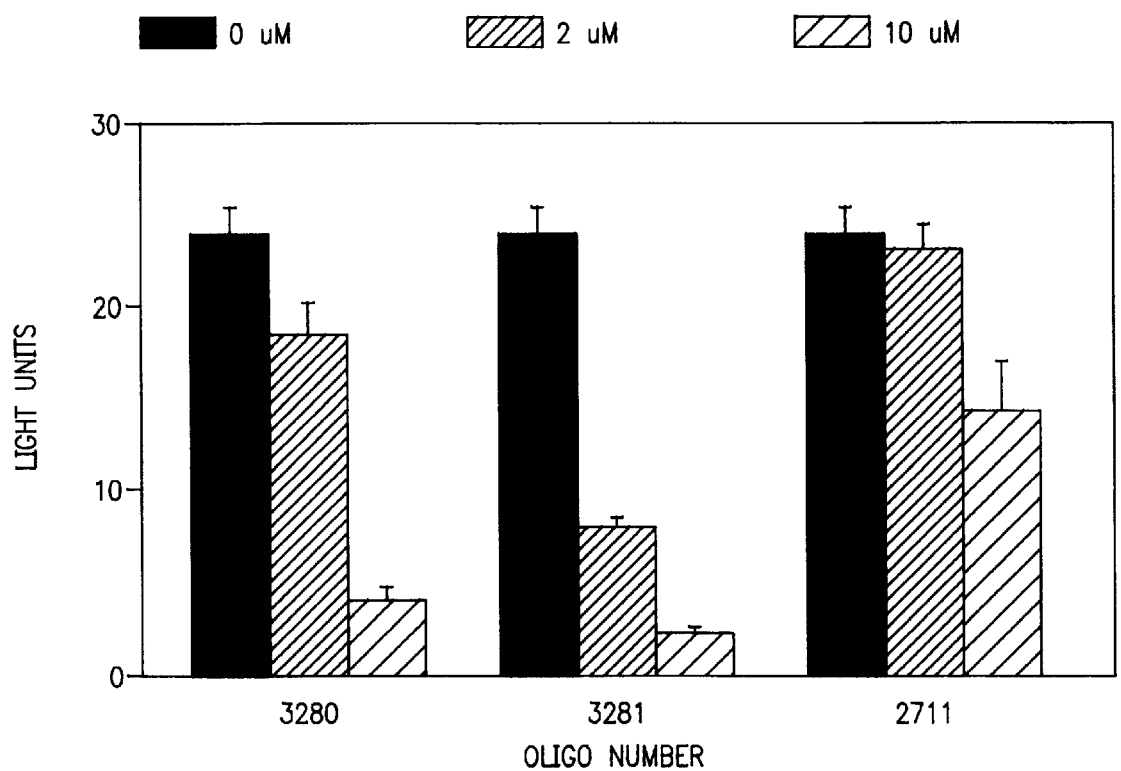
FIG. 7 is a bar graph showing antisense oligonucleotide inhibition of transactivation demonstrated by transient cellular assay.

The 2'-O-methyl oligonucleotides ISIS 3280 and 3281 were assayed for ability to inhibit transactivation in HeLa cells through binding to TAR. The transient transactivation assay was conducted as described in Example 1. Results are shown in FIG. 7; both 2'-O-methyl oligonucleotides inhibit transactivation in cells in a dose-dependent manner. ISIS 3281 inhibited transactivation in cells by 91%; ISIS 3280 inhibited transactivation by 83%. In another experiment, the 12-nucleotide 2'-O-methyl oligonucleotides ISIS 2523 and ISIS 2697 inhibited transactivation in cells by 75% and 38%, respectively.

Example 6

Figure 8A:
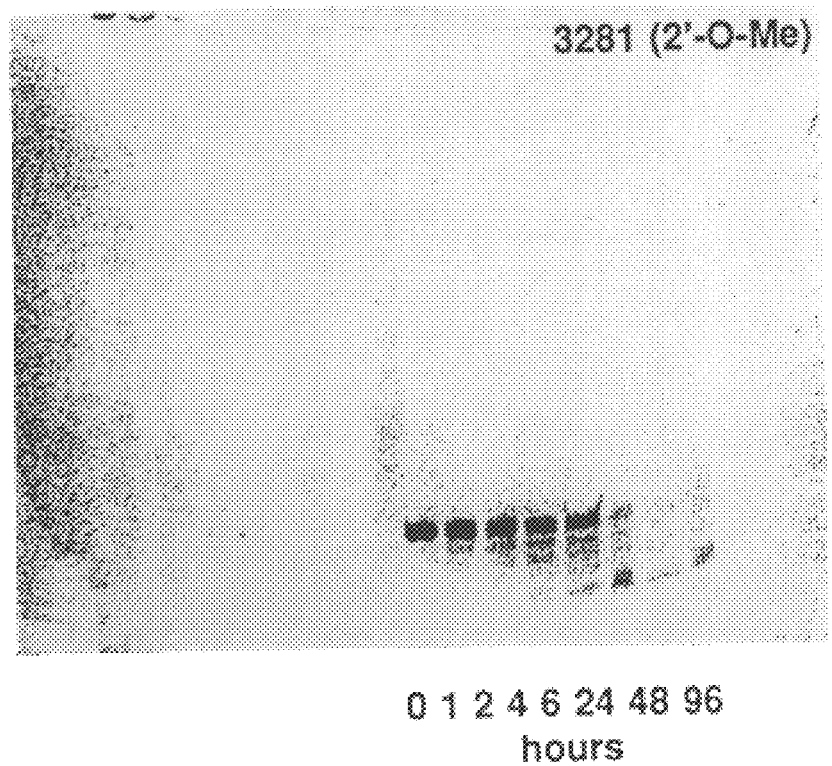
FIG. 8 shows three polyacrylamide gels demonstrating stability of oligonucleotides to serum nucleases.
Figure 8B:
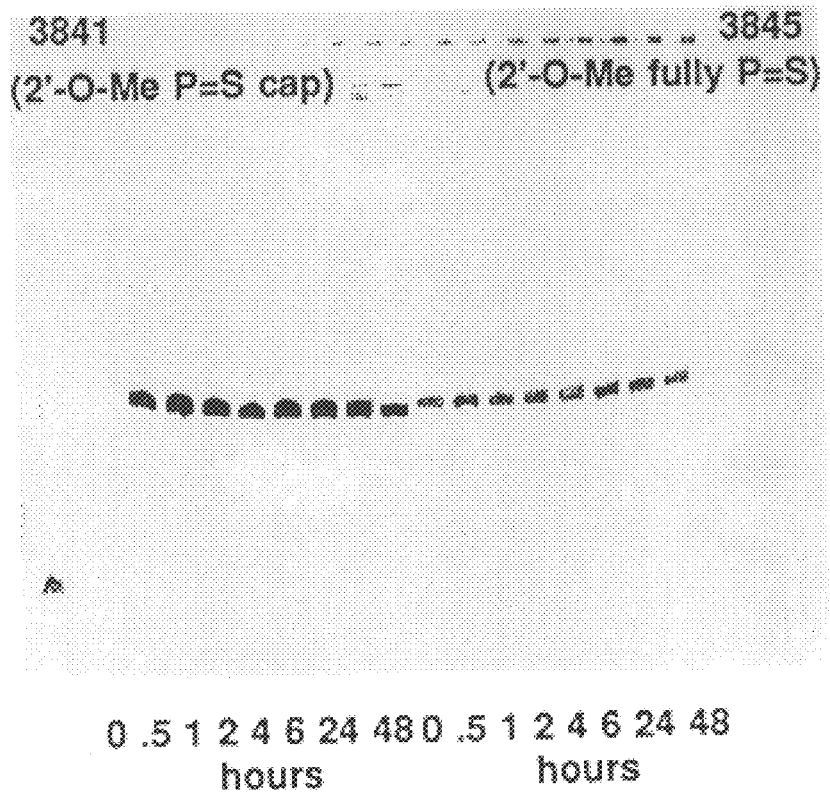
Figure 8C:
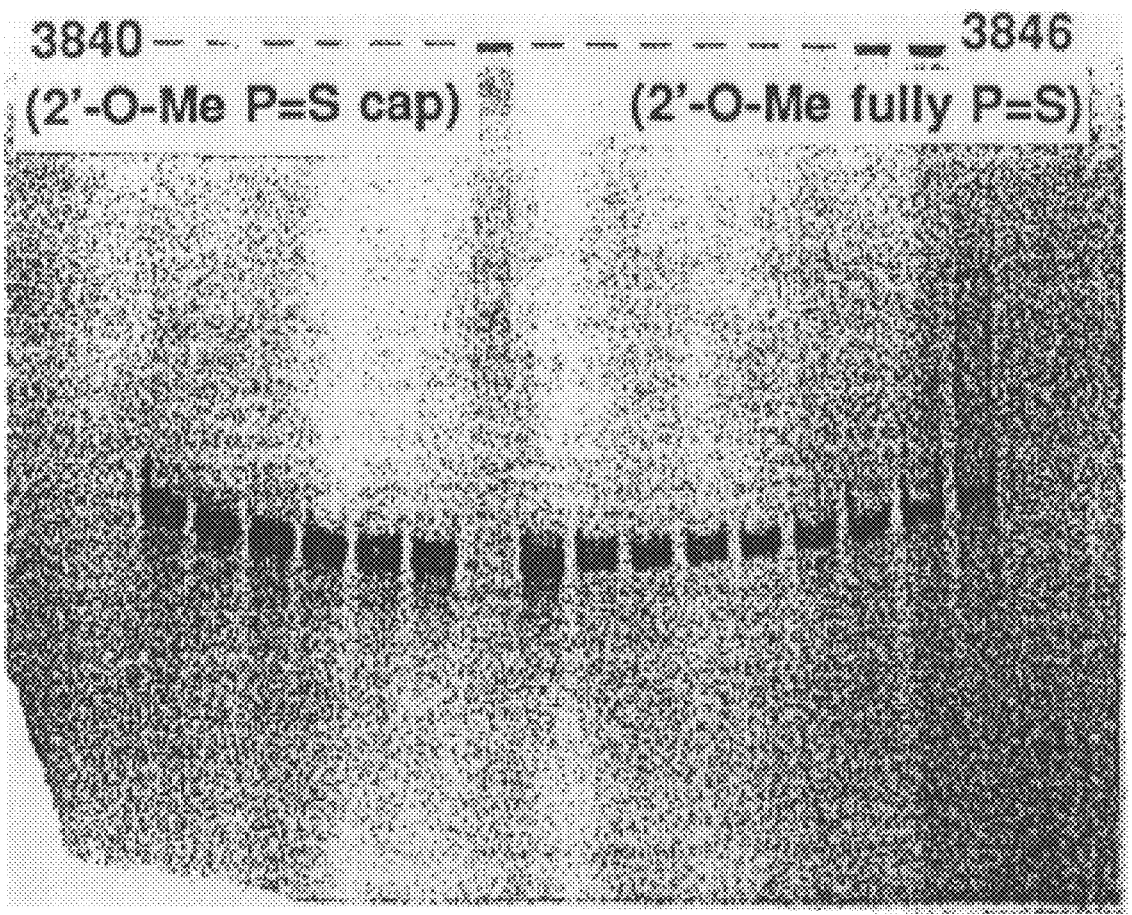

Nuclease Resistance of 2'-O-alkyl Oligonucleotides:

Unmodified phosphodiester oligonucleotides suffer from a susceptibility to nucleases, rendering them unstable. The 2'-O-methylated oligonucleotides of this invention were assayed for their resistance to nuclease degradation. Oligonucleotides (10 µM) were incubated in 10% fetal calf serum, a good source of nucleases, at 37° C. for long periods of time. Results are shown in Table 4 and FIG. 8.

TABLE 4

Stability of 2'-O-Methyl Oligonucleotides to Nucleases

| Oligonucleotide # | Modification | T½ |
|---|---|---|
| 3280 | 2'-O-methyl | >>48 hr |
| 3281 | 2'-O-methyl | 24 hr |
| 3840 | 2'-O-methyl; 3' P=S cap | >>48 hr |
| 3841 | 2'-O-methyl; 3' P=S cap | >>48 hr |
| 3845 | 2'-O-methyl; fully P=S | >>72 hr |
| 3846 | 2'-O-methyl; fully P=S | >>72 hr |

"3' P=S cap" indicates that only the three phosphodiester linkages at the 3' end of the oligonucleotide are replaced with phosphorothioates It can be seen from these data that the stability of 2'-O-methyl oligonucleotides is extremely good. The stability of double-modified 2'-O-methyl phosphorothioate oligonucleotides is even better, well over 72 hours.

What is claimed is:

1. An oligonucleotide having a nucleotide sequence selected from the group consisting of SEQ. ID. No. 1, SEQ. ID. No. 2, SEQ. ID. No. 3, SEQ. ID. No. 5, SEQ. ID. No. 6, SEQ. ID. No. 7, SEQ. ID. No. 8, and SEQ. ID. No. 9 and at least one $C_1$ to $C_9$ alkyl or benzyl 2'-O-modification.

2. An oligonucleotide of claim 1 having at least one phosphorothioate modification.

3. An oligonucleotide of claim 1 in a pharmaceutically acceptable carrier.

4. An oligonucleotide of claim 2 in a pharmaceutically acceptable carrier.

5. The oligonucleotide of claim 1 wherein substantially all 2' positions are modified with said modifications.

6. The oligonucleotide of claim 1 wherein substantially all 2' positions are modified with O-methyl groups.

7. The oligonucleotide of claim 1 wherein substantially all 2' positions are modified with O-methyl groups and substantially all internucleoside linkages are phosphorothioates.

* * * * *

UNITED STATES PATENT AND TRADEMARK OFFICE
CERTIFICATE OF CORRECTION

PATENT NO. : 6,034,233                                                                              Page 1 of 2
DATED : March 7, 2000
INVENTOR(S) : Ecker et al.

It is certified that error appears in the above-identified patent and that said Letters Patent is hereby corrected as shown below:

On the Title Page,

Under Related U.S. Application Data, please delete "07/578,929" and insert therefor --"07/518,929"

At Col. 1, line 47, please delete "MRNA" and insert therefor --mRNA--

At. Col. 2, Line 49, please delete "MRNA" and insert therefor --mRNA--

At. Col. 6, Line 39, please delete "O(CH$_2$)nCH$_3$ and insert therefor --O(CH$_2$)$_n$CH$_3$ At. Col. 8, Line 3, please delete "qap" and insert therefor --gag--

At. Col. 10, Line 37, please delete "MRNA" and insert therefor --mRNA--

At. Col.12, Line 34, please delete "PHIVPAP" and insert therefor --"pHIVPAP"

At. Col. 14, Line 31, please delete "$^{31}$p" and insert therefor --$^{31}$P--

UNITED STATES PATENT AND TRADEMARK OFFICE
CERTIFICATE OF CORRECTION

PATENT NO. : 6,034,233

DATED : March 7, 2000

INVENTOR(S) : Ecker et al.

It is certified that error appears in the above-identified patent and that said Letters Patent is hereby corrected as shown below:

In Table 1, line 1720, please delete "F=S" and insert therefor --P=S--

Table 3 heading is entered in duplicate

Signed and Sealed this

Twenty-seventh Day of March, 2001

Attest:

NICHOLAS P. GODICI

Attesting Officer

Acting Director of the United States Patent and Trademark Office

```
                          SEQUENCE LISTING (1) GENERAL INFORMATION:

(iii) NUMBER OF SEQUENCES:  9

(2) INFORMATION FOR SEQ ID NO: 1:

(i) SEQUENCE CHARACTERISTICS:
        (A) LENGTH: 18
        (B) TYPE:  nucleic acid
        (C) STRANDEDNESS:  single
        (D) TOPOLOGY:  linear (iv) ANTI-SENSE:  yes (xi) SEQUENCE DESCRIPTION:  SEQ ID NO: 1:

GCTCCCAGGC TCAGATCT                                                       18

(2) INFORMATION FOR SEQ ID NO: 2:

(i) SEQUENCE CHARACTERISTICS:
        (A) LENGTH: 26
        (B) TYPE:  nucleic acid
        (C) STRANDEDNESS:  single
        (D) TOPOLOGY:  linear (iv) ANTI-SENSE:  yes (xi) SEQUENCE DESCRIPTION:  SEQ ID NO: 2:

GCCAGAGAGC TCCCAGGCTC AGATCT                                              26

(2) INFORMATION FOR SEQ ID NO: 3:

(i) SEQUENCE CHARACTERISTICS:
        (A) LENGTH: 28
        (B) TYPE:  nucleic acid
        (C) STRANDEDNESS:  single
        (D) TOPOLOGY:  linear (iv) ANTI-SENSE:  yes (xi) SEQUENCE DESCRIPTION:  SEQ ID NO: 3:

CCAGAGAGCT CCCAGGCTCA GATCTGGT                                            28

(2) INFORMATION FOR SEQ ID NO: 4:

(i) SEQUENCE CHARACTERISTICS:
        (A) LENGTH: 26
        (B) TYPE:  nucleic acid
```

(C) STRANDEDNESS:  single
            (D) TOPOLOGY:  linear (iv) ANTI-SENSE:  yes (xi) SEQUENCE DESCRIPTION:  SEQ ID NO: 4:

GCCAGAGAGC TCCCAGGCTC AGATCT                                          26

(2) INFORMATION FOR SEQ ID NO: 5:

(i) SEQUENCE CHARACTERISTICS:
            (A) LENGTH: 12
            (B) TYPE:  nucleic acid
            (C) STRANDEDNESS:  single
            (D) TOPOLOGY:  linear (iv) ANTI-SENSE:  yes (xi) SEQUENCE DESCRIPTION:  SEQ ID NO: 5:

GAGCUCCCAG GC                                                         12

(2) INFORMATION FOR SEQ ID NO: 6:

(i) SEQUENCE CHARACTERISTICS:
            (A) LENGTH: 12
            (B) TYPE:  nucleic acid
            (C) STRANDEDNESS:  single
            (D) TOPOLOGY:  linear (iv) ANTI-SENSE:  yes (xi) SEQUENCE DESCRIPTION:  SEQ ID NO: 6:

CCCAGGCUCA GA                                                         12

(2) INFORMATION FOR SEQ ID NO: 7:

(i) SEQUENCE CHARACTERISTICS:
            (A) LENGTH: 17
            (B) TYPE:  nucleic acid
            (C) STRANDEDNESS:  single
            (D) TOPOLOGY:  linear (iv) ANTI-SENSE:  yes (xi) SEQUENCE DESCRIPTION:  SEQ ID NO: 7:

AGAGAGCUCC CAGGCUC                                                    17

(2) INFORMATION FOR SEQ ID NO: 8:

(i) SEQUENCE CHARACTERISTICS:
            (A) LENGTH: 17
            (B) TYPE:  nucleic acid
            (C) STRANDEDNESS:  single
            (D) TOPOLOGY:  linear (iv) ANTI-SENSE:  yes (xi) SEQUENCE DESCRIPTION:  SEQ ID NO: 8:

CUCCCAGGCU CAGAUCU                                                    17

(2) INFORMATION FOR SEQ ID NO: 9:

(i) SEQUENCE CHARACTERISTICS:
            (A) LENGTH: 17
            (B) TYPE:  nucleic acid
            (C) STRANDEDNESS:  single
            (D) TOPOLOGY:  linear (iv) ANTI-SENSE:  yes (xi) SEQUENCE DESCRIPTION: SEQ ID NO: 9:

GAGCUCCCAG GCUCAGA                                                                                         17